US009603987B2

(12) United States Patent
Brandl et al.

(10) Patent No.: US 9,603,987 B2
(45) Date of Patent: Mar. 28, 2017

(54) METHOD AND DEVICE FOR CONVEYING FLUIDS INTO THE TREATMENT UNIT OF A MEDICAL TREATMENT APPARATUS, IN PARTICULAR INTO THE DIALYZER OF A DIALYSIS APPARATUS

(75) Inventors: Matthias Brandl, Bad Koenigshofen (DE); Manfred Weis, St. Wendel (DE); Volker Nier, Reichelsheim (DE); Gerhard Mager, Bad Homburg (DE); Michael Herrenbauer, Neu-Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 545 days.

(21) Appl. No.: 13/703,691

(22) PCT Filed: Jun. 14, 2011

(86) PCT No.: PCT/EP2011/002915
§ 371 (c)(1),
(2), (4) Date: Dec. 12, 2012

(87) PCT Pub. No.: WO2011/157396
PCT Pub. Date: Dec. 22, 2011

(65) Prior Publication Data
US 2013/0087210 A1 Apr. 11, 2013

(30) Foreign Application Priority Data
Jun. 14, 2010 (DE) .................... 10 2010 023 635

(51) Int. Cl.
*A61M 1/16* (2006.01)
*A61M 1/36* (2006.01)

(52) U.S. Cl.
CPC .......... *A61M 1/3624* (2013.01); *A61M 1/165* (2014.02); *A61M 1/1635* (2014.02);
(Continued)

(58) Field of Classification Search
CPC .. A61M 1/1635; A61M 1/165; A61M 1/1694; A61M 1/3624; Y10T 137/0324; Y10T 137/2574
See application file for complete search history.

(56) References Cited

U.S. PATENT DOCUMENTS

| 4,209,391 A | 6/1980 | Landau et al. |
| 4,770,769 A | 9/1988 | Schael |
| 2009/0198170 A1 | 8/2009 | Childers et al. |

FOREIGN PATENT DOCUMENTS

| DE | 2838414 A1 | 3/1980 |
| DE | 42 39 937 A1 | 6/1994 |

(Continued)

OTHER PUBLICATIONS

English translation German Patent Application No. 19702211 A1 (Jul. 1998).*

(Continued)

*Primary Examiner* — John Kim
(74) *Attorney, Agent, or Firm* — Kilyk & Bowersox, P.L.L.C.

(57) ABSTRACT

The present invention relates to a device and method for conveying fluids into the treatment unit of a medical treatment apparatus. The device and method according to the present invention are based on the fact that the fluid with which the treatment unit is supplied, circulates in a fluid circuit including the treatment unit. To balance fresh and used fluid fed to the treatment unit or conveyed from the treatment unit, a balancing unit with a balancing chamber is used, which can be incorporated into the fluid circuit including the treatment unit. It is thus possible to supply the fluid circuit continuously with fresh fluid or to carry away used fluid continuously from the fluid circuit. The supply and discharge of fresh and used fluid can take place at a different (Continued)

flow rate from the flow rate at which the fluid circulates in the fluid circuit via the treatment unit.

12 Claims, 3 Drawing Sheets

(52) U.S. Cl.
CPC ...... *A61M 1/1694* (2013.01); *Y10T 137/0324* (2015.04); *Y10T 137/2574* (2015.04)

(56) References Cited

FOREIGN PATENT DOCUMENTS

| | | |
|---|---|---|
| DE | 69400279 T2 | 11/1996 |
| DE | 19702211 A1 | 7/1998 |
| DE | 29902953 U1 | 7/2000 |
| EP | 1029554 A2 | 8/2000 |
| EP | 2 005 982 A1 | 12/2008 |
| WO | 9510311 A1 | 4/1995 |

OTHER PUBLICATIONS

International Preliminary Report on Patentability from PCT/EP2011/002915 mailed on Dec. 27, 2012.
International Search Report from PCT/EP2011/002915 mailed on Oct. 21, 2011.

\* cited by examiner

METHOD AND DEVICE FOR CONVEYING FLUIDS INTO THE TREATMENT UNIT OF A MEDICAL TREATMENT APPARATUS, IN PARTICULAR INTO THE DIALYZER OF A DIALYSIS APPARATUS

CROSS REFERENCE TO RELATED APPLICATIONS

This is a 371 national phase application of PCT/EP2011/002915 filed Jun. 14, 2011, which claims priority from German Patent Application No. 10 2010 023 635.7, filed Jun. 14, 2010.

FIELD OF INVENTION

The present invention relates to a device and a method for conveying fluids into the treatment unit of a medical treatment apparatus, in particular into the dialyzer of a dialysis apparatus. Moreover, the present invention relates to an extracorporeal blood treatment apparatus, in particular a dialysis apparatus, which comprises a device for conveying fluids into the treatment unit, in particular the dialyzer, of the blood treatment apparatus, in particular dialysis apparatus.

BACKGROUND OF INVENTION

Various kinds of treatment apparatuses are known that comprise a treatment unit to be supplied with a fluid. The known treatment apparatuses include, for example, blood treatment apparatuses. During the blood treatment, the patient's blood flows in an extracorporeal blood circuit through the blood treatment unit. In the case of apparatuses for hemodialysis, hemofiltration and hemodiafiltration, the blood treatment unit is a dialyzer or filter, which is divided by a semi-permeable membrane into a blood chamber and a dialyzing fluid chamber. During the dialysis treatment, the blood flows in an extracorporeal blood circuit through the blood chamber, whilst the dialyzing fluid flows in a dialyzing fluid circuit through the dialyzing fluid chamber of the dialyzer.

On account of the large exchange quantities, there is a need with the known methods and apparatuses for blood treatment for an exact balancing of the fluid removed from the patient and the fluid fed to the patient during the overall treatment time. Gravimetric and volumetric balancing devices belong to the prior art.

A hemodiafiltration apparatus with volumetric balancing is known for example from DE 26 34 238 A1. The balancing device of the known hemodiafiltration apparatus comprises a volume-rigid hollow body, which is divided by a mobile partition wall into two chambers. Each chamber comprises an inlet and an outlet, on which supply lines and discharge lines for fresh and, respectively, used dialyzing fluid are disposed, a shut-off element being incorporated in each line. Moreover, provision is made for pumps for conveying the fresh and used dialyzing fluid as well as a control unit, which permits a mutual filling of the two chambers.

In order to be able to ensure a continuous flow of dialyzing fluid through the dialyzing fluid chamber of the dialyzer, two balancing chamber are connected in parallel in practice, said balancing chambers supplying the dialyzer alternately with fresh dialyzing fluid. A balancing unit with two balancing chambers is known for example from DE 28 38 414.

During a dialysis treatment, the dialyzing fluid flow typically amounts to 500 ml/min, but can amount to up to 1000 ml/min depending on the given treatment situation. In the case of a dialysis period of 4 hours, this means a dialyzing fluid requirement which typically amounts to between 120 L, but depending on the given treatment situation can also be over 200 L.

On account of the large fluid requirement in dialysis, the preparation of the dialysate from concentrates and pure water (RO water) in the machine has become established, in order to avoid the storage of fairly large quantities of solutions. The RO water is made available centrally in the clinic and distributed via lines to the dialysis machines in the dialysis stations.

In the treatment of an acute renal insufficiency, such as can occur for example after accidents, which calls for intensive-care support for the patient, a RO water connection is generally not present. The dialyzing fluid is then made available to the machine by means of containers, for example canisters or bags.

In order to keep the handling costs down, an attempt is made, especially in the case of intensive-care support for acute renal insufficiency, to reduce the requirement for dialyzing fluid. This is achieved by the fact that the dialyzing fluid is recirculated via the dialyzer for a certain length of time. The dialysate requirement can thus be reduced to values which lie below 100 ml/min.

A blood treatment apparatus with a recirculation circuit is known for example from U.S. Pat. No. 5,685,988. The recirculation of dialyzing fluid should however only be used for the determination of blood treatment parameters.

The problem underlying the present invention is to provide a device for conveying fluids into the treatment unit of a medical treatment apparatus, in particular into the dialyzer of a dialysis apparatus, with which device the requirement for dialyzing fluid can be reduced. A further problem of the present invention is to provide a method for conveying fluids into the blood treatment unit of a medical treatment apparatus, said method permitting a reduction in the requirement for dialyzing fluid. The problem of the present invention is also to provide an extracorporeal blood treatment apparatus with such a device for conveying fluids.

The device according to the present invention and the method according to the present invention are based on the fact that the fluid with which the treatment unit is supplied circulates in a fluid circuit which includes the treatment unit. In order to balance fresh and used fluid which is fed to the treatment unit or carried away from the treatment unit, use is made of a balancing unit which in principle can comprise one or two balancing chambers.

The device according to the present invention and the method according to the present invention are characterised in that the balancing chamber of the balancing unit, or the two balancing chambers of the balancing unit, can be incorporated into the fluid circuit including the treatment unit. It is thus possible to supply fresh fluid continuously to the fluid circuit and to discharge used fluid continuously from the fluid circuit. The supply and discharge of fresh and used fluid can take place at a flow rate different from the flow rate at which the fluid circulates via the treatment unit in the fluid circuit. Consequently, there becomes established in the fluid circuit a "fluid" which, depending on the ratio of the flow rates, lies in concentration between a "fresh fluid" and a "used fluid". Independently of the supply and discharge of fresh or used fluid, fluid (ultrafiltrate) can also be removed from the fluid circuit including the blood treatment unit, in particular the dialyzer.

In a preferred embodiment of the present invention, the flow rate at which the fluid circulates via the treatment unit in the fluid circuit is greater than the flow rate at which fluid is fed to and discharged from the fluid circuit.

The device according to the present invention comprises a bypass, which connects the discharge line leading from the balancing chamber to the treatment unit to the supply line leading from the treatment unit to the balancing chamber. The bypass permits not only a continuous supply of fresh fluid into the fluid circuit including the treatment unit, but also the maintenance of a fluid flow through the blood treatment unit when the balancing chamber of the balancing unit is being filled with fresh fluid, thereby displacing used fluid. If a balancing chamber with two alternately operating balancing chambers is used, this advantage is admittedly not brought to bear. A particularly preferred embodiment of the present invention thus provides a balancing unit with only one balancing chamber. In this particularly preferred embodiment, the bypass ensures that the fluid flow through the blood treatment unit is not interrupted during the switch-over of the balancing chambers. A simplified design of the balancing unit thus results.

The means for conveying fluid into or out of the balancing chamber and the means for interrupting the supply of fluid into the balancing chamber or the discharge of fluid out of the balancing chamber can be designed differently. The known occluding pumps, into which hose lines can be inserted, are preferably used for conveying fluid. For the interruption of the supply or discharge of fluid, use is preferably made of the known electromagnetically or pneumatically operated shut-off elements, which are disposed in the lines. A control unit controls the means for conveying fluid and the means for interrupting the supply or discharge of fluid. Since occluding pumps pinch off the hose line in the standstill state, the occluding pumps can also replace shut-off elements.

In a particularly preferred embodiment, the means for conveying fluid comprises a first pump, which is disposed in the supply line leading from the fluid source to the balancing chamber. Moreover, the conveying means comprises two further pumps, which are disposed in the discharge line leading from the balancing chamber to the blood treatment unit. Of these two pumps, one is disposed in the section of this discharge line which leads to the point at which one connection of the bypass is connected to the discharge line, whilst the other pump is disposed in the section of this discharge line which leads away from the connection point of the bypass. The flow rates of these two pumps in the discharge line determine the flow rate at which fresh fluid is fed to the fluid circuit and used fluid is carried away from the fluid circuit.

In a particularly preferred embodiment, the means for interrupting the supply and/or discharge of fluid comprise a first shut-off element, which is disposed in the first supply line leading from the fluid source to the balancing chamber, a second shut-off element, which is disposed in the second discharge line leading away from the balancing chamber and leading to the drain, a third shut-off element, which is disposed in the second discharge line leading away from the balancing chamber and leading to the blood treatment unit, and a fourth shut-off element, which is disposed in the second supply line leading from the treatment unit to the balancing chamber. All the shut-off elements are controlled by the control unit.

In the particularly preferred embodiment, the control unit is designed such that the first and second shut-off elements are opened and the third and fourth shut-off elements are closed in a first work step of a first work cycle of successive work cycles, the first and third pumps being in operation. In the first work step, the balancing chamber is filled with fresh fluid, used fluid thereby being displaced. During the filling procedure of the balancing chambers, the fluid flow through the treatment unit is not interrupted. The first work step is followed by a second work step, in which the first and second shut-off elements are closed and the third and fourth shut-off elements are opened, the second and third pumps being in operation. In the second work step, the fluid circulates in the fluid circuit including the blood treatment unit. Fresh fluid can also be, but does not have to be, fed to the fluid circuit or carried away from the fluid circuit.

A further preferred embodiment provides for the integration of a further shut-off element in the bypass. This shut-off element serves for the better filling and venting of the system before the treatment is carried out. On the other hand, the circulation in the fluid circuit can also be interrupted with the shut-off element in the bypass.

BRIEF DESCRIPTION OF THE DRAWINGS

Examples of embodiments of the present invention are explained below in detail by reference to the drawings.

In the figures.

DETAILED DESCRIPTION

Figure 1:
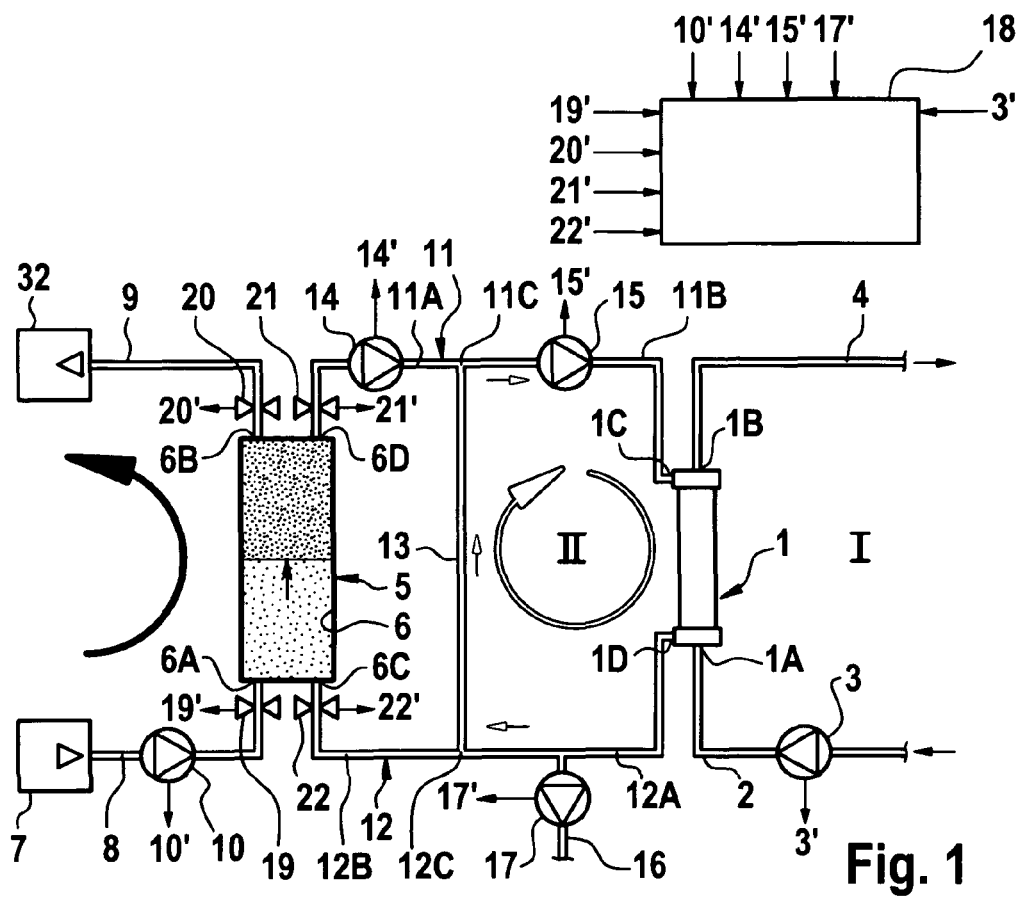
FIG. 1 shows a hemodialysis apparatus with a device for supplying the dialyzer of the dialysis apparatus with dialyzing fluid in a very simplified schematic representation, wherein the first work step of a work cycle is represented.

The present invention is described below using the example of a blood treatment apparatus which comprises a dialyzer as a blood treatment unit. FIG. 1 shows the main components of the hemodialysis apparatus in a very simplified schematic representation. The device for supplying the dialyzer with dialyzing fluid is a component part of the dialysis apparatus.

The dialysis apparatus comprises a dialyzer 1, which is divided by a semi-permeable membrane (not represented) into a blood chamber (not represented) and a dialyzing fluid chamber. A blood supply line 2, into which a blood pump 3 is incorporated, leads from the patient to an inlet 1A of the blood chamber of dialyzer 1, whilst a blood discharge line 4, which leads to the patient, leads away from an outlet 1B of the blood chamber of dialyzer 1. During the blood treatment, the patient's blood flows in extracorporeal blood circuit I through the blood chamber of dialyzer 1.

Dialyzer 1 is supplied with dialyzing fluid, which flows through the dialyzing fluid chamber of dialyzer 1. The device for conveying the dialyzing fluid into dialyzer 1 is described below.

For the balancing of fresh dialyzing fluid against used dialyzing fluid, use is made of a balancing unit 5 which, in the present example of embodiment, comprises only one balancing chamber 6. Balancing chamber 6 comprises a first inlet 6A at the underside and a first outlet 6B at the upper side as well as a second inlet 6C at the underside and a second outlet 6D at the upper side.

The dialyzing fluid is made available in a dialyzing fluid source 7, which can be a canister or a bag. Leading away from dialyzing fluid source 7 is a first supply line 8, which leads to first inlet 6A of balancing chamber 6. Leading away from first outlet 6B of balancing chamber 6 is a first discharge line 9, which leads to a drain 32. Incorporated into first supply line 8 is a blood pump 10, in particular an occluding pump, which conveys fresh dialyzing fluid from dialyzing fluid source 7 into balancing chamber 6.

Leading away from second outlet 6D of balancing chamber 6 is a second discharge line 11, which leads to inlet 1C of the dialyzing fluid chamber of dialyzer 1. Leading away from outlet 1D of the dialyzing fluid chamber of dialyzer 1 is a second supply line 12, which leads to second inlet 6C of balancing chamber 6.

Supply lines and discharge lines 8, 9, 11, 12 are hose lines. Second discharge line 11 comprises, in the flow direction, a first section 11A and a second section 11B, whilst second supply line 12 comprises, in the flow direction, a first section 12A and a second section 12B.

Second discharge line 11 and second supply line 12 are connected via a bypass 13. Bypass 13 is a line which is connected with one end to junction point 11C between first section 11A and second section 11B of second discharge line 11 and with the other end to junction point 12C between first section 12A and second section 12B of second supply line 12. A fluid circuit II, which includes the dialyzing fluid chamber of dialyzer 1, is created with bypass 13. Fluid circuit II comprises bypass line 13, second section 11B of second discharge line 11, the dialyzing fluid chamber of dialyzer 1 and first section 12A of second supply line 12.

A second pump 14 is incorporated into first section 11A of second discharge line 11 and a third pump 15 is incorporated into second section 11B of second discharge line 11. Leading away from first section 12A of second supply line 12 is an ultrafiltrate line 16, into which a fourth pump 17 is incorporated, with which fluid (ultrafiltrate) can be withdrawn from fluid circuit II. The four pumps 10, 14, 15, 17 are connected via control lines 10', 14', 15', 17' to a control unit 18. In the present example, control unit 18 is a component part of the central control unit of the dialysis apparatus. Central control unit 18 of the dialysis apparatus is also connected to blood pump 3 via a control line 3'.

A first shut-off element 19 is incorporated into first supply line 8 between first pump 10 and balancing chamber 6, whilst a second shut-off element 20 is incorporated into first discharge line 9. A third shut-off element 21 is incorporated into second discharge line 11 between balancing chamber 6 and second pump 14, whilst a third shut-off element 22 is incorporated into second supply line 12 between junction point 12C and balancing chamber 6. Shut-off elements 19, 20, 21, 22 are electromagnetically operated hose clamps, which are connected via control lines 19', 20', 21', 22' to central control unit 18.

Figure 2:
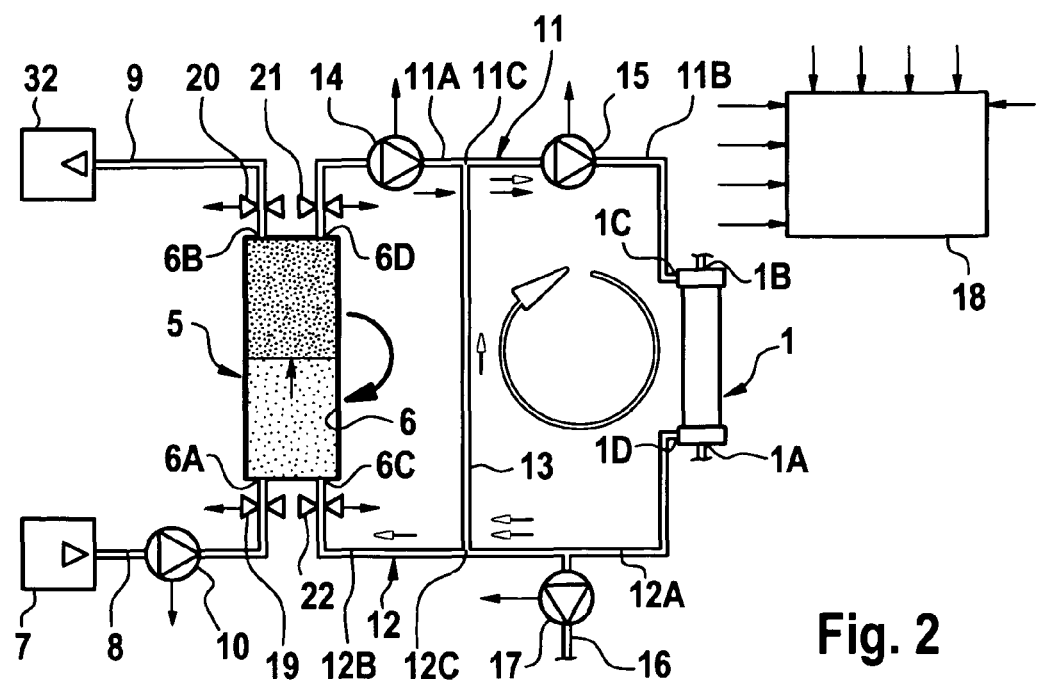
FIG. 2 shows the hemodialysis apparatus of FIG. 2, wherein the second work step of the work cycle is represented.

Central control unit 18 controls pumps 10, 14, 15 as follows. The dialysis apparatus is operated in successive cycles, which each comprise two work steps. FIG. 2 shows the first work step and FIG. 2 the second work step of a work cycle.

The first work step comprises the filling of balancing chamber 6, while dialyzing fluid is flowing through dialyzer 1. Central control unit 18 opens first and second shut-off elements 19, 20 and closes third and fourth shut-off elements 21, 22. Control unit 18 thereby puts first pump 10 and third pump 15 into operation. Second pump 14 is at a standstill. Since second occluding pump 14 is at a standstill, third shut-off element 21 can also be open.

First pump 10 conveys fresh dialyzing fluid out of dialyzing fluid source 7 into balancing chamber 6, which has been filled with used dialyzing fluid in the second work step of the preceding work cycle. While balancing chamber 6 is being filled with fresh dialyzing fluid, the used dialyzing fluid is displaced via a first discharge line 9 into drain 32. First pump 10 runs until such time as used dialyzing fluid has been completely replaced by fresh dialyzing fluid in balancing chamber 6. During the filling of balancing chamber 6 with fresh dialyzing fluid, the fluid flow through dialyzer 1 is not interrupted. Third pump 15 conveys the dialyzing fluid in fluid circuit II, which includes second section 11B of second discharge line 11, dialyzer 1, first section 12A of second supply line 12 and bypass line 13. Balancing chamber 6 should be filled as quickly as possible with fresh dialyzing fluid, so that the dialyzing fluid circulates for only a short period in the fluid circuit (FIG. 1A).

The first work step (FIG. 1) is followed by the second work step (FIG. 2). Central control unit 18 closes first and second shut-off elements 19, 20 and opens third and fourth shut-off elements 21, 22 in the second work step. Furthermore, control unit 18 stops first pump 10 and puts second pump 14 into operation. Consequently, second and third pumps 14, 15 are running. Control unit 18 selects a smaller delivery rate for second pump 14 than for third pump 15. Consequently, dialyzing fluid flows in fluid circuit II at a flow rate which corresponds to the difference between the flow rates of third and second pumps 15, 14. This flow rate $QD_{fast}$ can be relatively high.

While dialyzing fluid is circulating in fluid circuit II through dialyzer 1, fresh dialyzing fluid is constantly fed to fluid circuit II and used dialyzing fluid removed from fluid circuit 12. The fresh dialyzing fluid is fed to fluid circuit II at the delivery rate preselected by second pump 14 via first section 11A of second discharge line 11, which is connected to second outlet 6D of balancing chamber 6. Used dialyzing fluid is withdrawn from fluid circuit II via second section 12B of second supply line 12, which is connected to second inlet 6C of balancing chamber 6. The dialysis apparatus also permits fluid (ultrafiltrate) to be withdrawn from fluid circuit II. Control unit 18 starts ultrafiltration pump 17 for the purpose of ultrafiltration.

Depending on the flow rates of second and third pumps 14, 15, fresh dialyzing fluid can be supplied continuously in a relatively short or a relatively long time and the desired ratio between fresh and used dialyzing fluid in fluid circuit II can be adjusted.

The second work step (FIG. 2) of the work cycle is then followed again by the first work step (FIG. 1) of a subsequent cycle.

Figure 3:
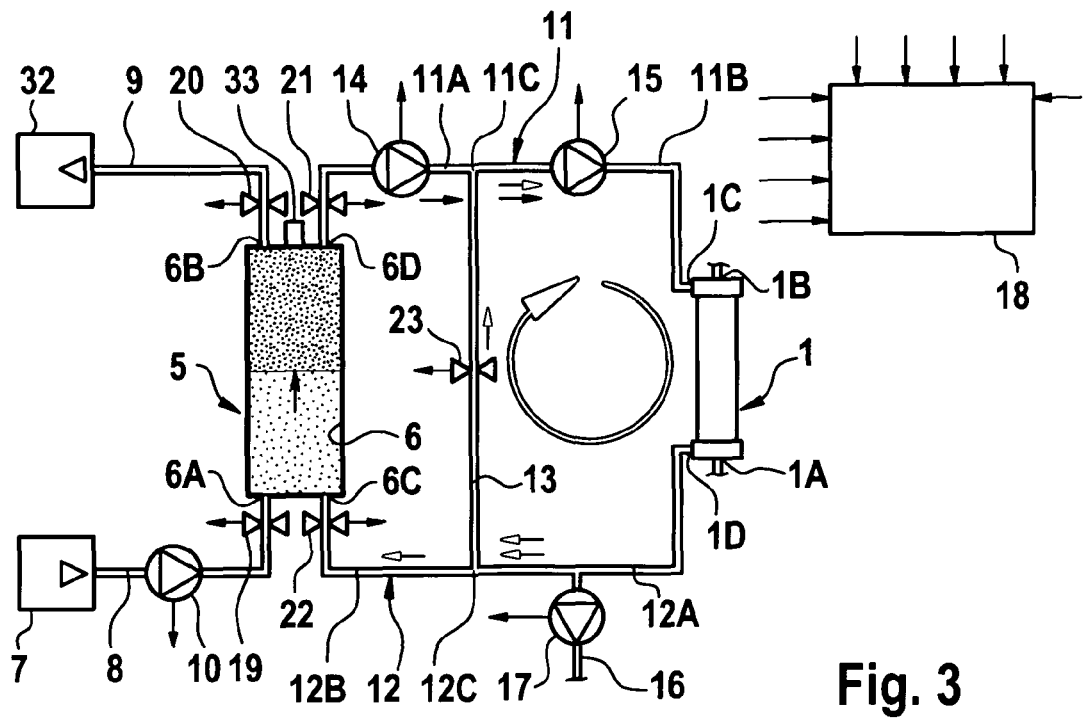
FIG. 3 shows a second example of embodiment of the hemodialysis apparatus with the device for supplying the dialyzer with dialyzing fluid in a very simplified schematic representation.

FIG. 3 shows a second example of embodiment of the dialysis apparatus, which differs from the embodiment described by reference to FIGS. 1 and 2 solely in that a fifth shut-off element 23, which is also operated by central control unit 18, is incorporated into bypass line 13. The parts corresponding to one another are therefore provided with the same reference numbers. Shut-off element 23 in bypass line 13 is in principle open during the operation of the dialysis apparatus. Shut-off element 23 can however also be closed in order to interrupt the circulation of the dialyzing fluid in fluid circuit II.

Shut-off element 23 in bypass line 13 is closed for the filling and venting of the fluid system, so that the fluid flow through the bypass line is interrupted. Furthermore, second shut-off element 20 is closed, so that fluid cannot pass into drain 32. The fluid is fed via a first supply line 8 to balancing chamber 6 while pump 10 is running. When pumps 14 and 15 are running, the fluid can flow through second discharge line 11, dialyzer 1 and second supply line 12. For the purpose of venting, a venting valve 33 is provided at the upper side of balancing chamber 6, which is represented only in outline in FIG. 3.

Figure 4:
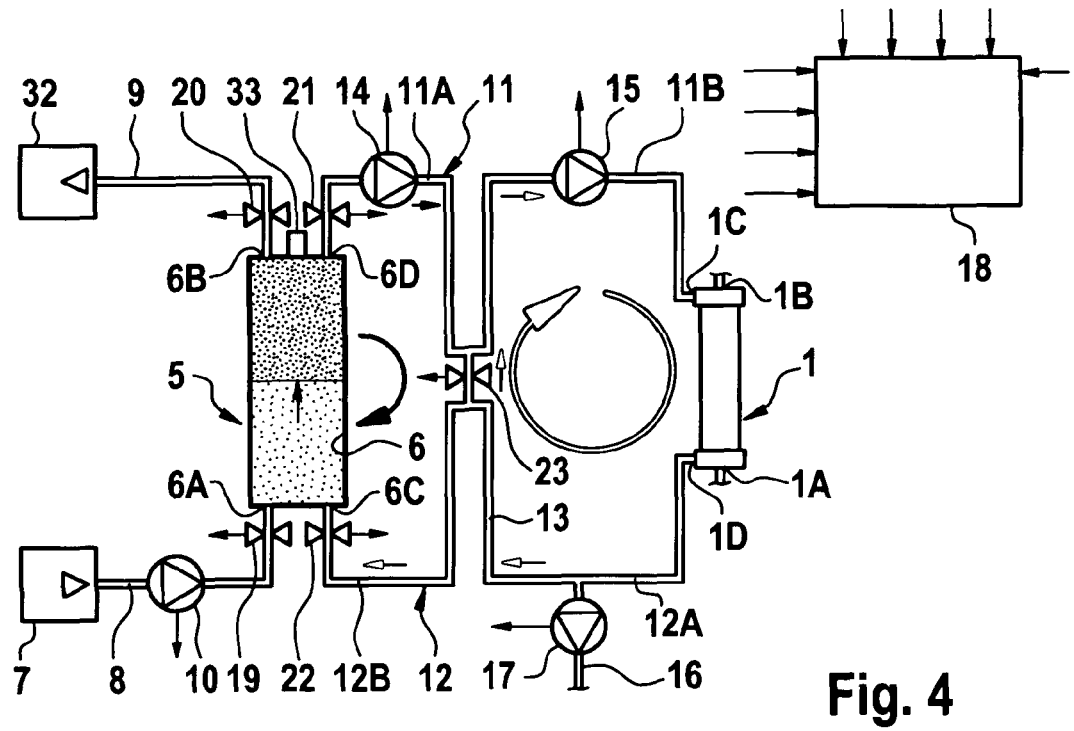
FIG. 4 shows an alternative embodiment of the hemodialysis apparatus of FIG. 3.

FIG. 4 shows an alternative embodiment of the dialysis apparatus of FIG. 3. The example of embodiment of FIG. 4 differs from the embodiment of FIG. 3 only by the routing of second discharge line 11 and second supply line 12 and the length of bypass line 13. The parts corresponding to one another are again provided with the same reference numbers. In order to reduce the dead volume, in which air could accumulate when the fluid system is being filled, second discharge line and supply line 11, 12 are led directly to the connections of shut-off element 23, so that the volume of bypass 13 can be reduced to a minimum.

The device according to the present invention for supplying the dialyzer with dialyzing fluid has the advantage that a balancing unit with two balancing chambers can be dispensed with. It is possible even with a balancing unit comprising only one balancing chamber to maintain a continuous flow of dialyzing fluid through the dialyzer during the balancing of fresh dialyzing fluid against used dialyzing fluid.

Figure 5:
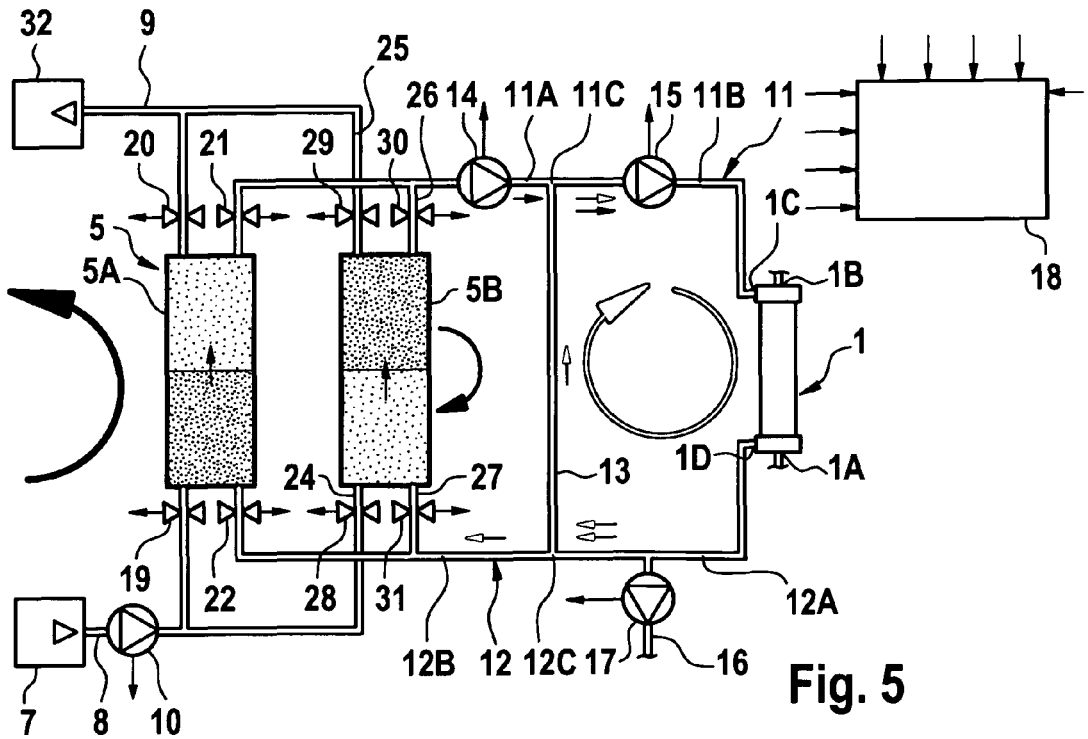
FIG. 5 shows a further example of embodiment of the dialysis apparatus in a very simplified schematic representation and FIG. 6 shows an alternative embodiment of the dialysis apparatus of FIG. 5.

For the sake of completeness, FIG. 5 shows a dialysis apparatus with two balancing chambers 6A, 6B which are connected in parallel and which operate alternately. The example of embodiment of FIG. 5 differs from the embodiment of FIG. 1 and FIG. 2 in that second balancing chamber 6B with respective supply lines and discharge lines 24, 25, 26, 27, into which shut-off elements 28, 29, 30, 31 are respectively incorporated, is connected in parallel to first balancing chamber 6A. Balancing unit 6 with two balancing chambers 6A, 6B is operated in a known manner, as is described for example in DE 28 38 414.

Figure 6:
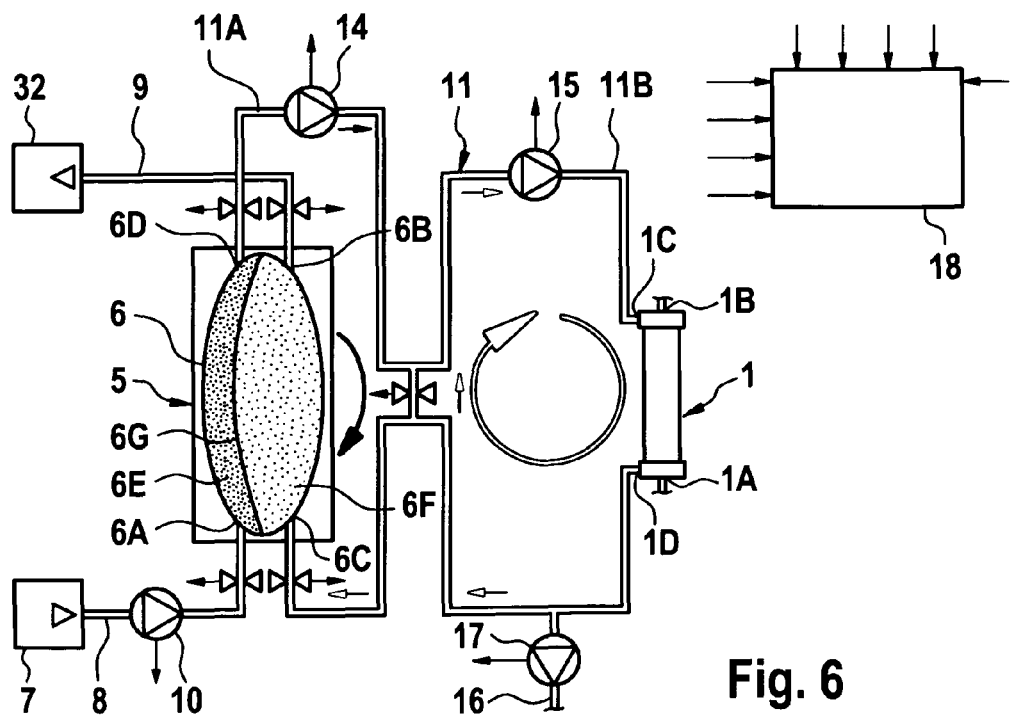

FIG. 6 shows a further example of embodiment, which differs from the embodiment of FIG. 4 solely in that balancing chamber 6 is divided by a flexible partition wall 6G into a first chamber half 6E and a second chamber half 6F. With this embodiment, first inlet 6A and second outlet 6D are connected to first chamber half 6E, whilst second inlet 6C and first outlet 6B are connected to second chamber half 6F. In this embodiment, the two chamber halves 6E and 6F of balancing chamber 6 are filled alternately with fresh and used dialyzing fluid. The parts corresponding to one another are again provided with the same reference numbers. With this embodiment, too, fluid circuit II permits the maintenance of the flow of dialyzing fluid through dialyzer 1 during the filling of balancing chamber 6 with fresh dialyzing fluid. When one of chamber halves 6E or 6F is being filled with fresh dialyzing fluid, the used dialyzing fluid is displaced from the respective other chamber half 6F or 6E.

What is claimed is:

1. A system for conveying fluid into a treatment unit of a medical treatment apparatus comprising:
    a balancing unit which comprises at least one balancing chamber,
    a first supply line leading to the balancing chamber for supplying fluid from a fluid source into the balancing chamber and a first discharge line leading away from the balancing chamber for discharging fluid from the balancing chamber into a drain,
    a second discharge line leading away from the balancing chamber for discharging fluid from the balancing chamber into the treatment unit and a second supply line leading to the balancing chamber for supplying fluid from the treatment unit into the balancing chamber,
    a conveying system for conveying fluid at least one of into or out of the balancing chamber and a supply interruption system for interrupting at least one of the supply of fluid into the balancing chamber or discharge of fluid from the balancing chamber,
    a control unit configured to control the conveying system and the supply interruption system; and,
    a bypass line connecting the second discharge line to the second supply line, such that a fluid circuit including the treatment unit is formed which completely or partially bypasses the balancing chamber,
    wherein the conveying system comprises:
        a first pump disposed in the first supply line;
        a second pump disposed in a first section of the second discharge line; and
        a third pump disposed in a second section of the second discharge line,
        wherein the bypass line extends between the first section and the second section of the second discharge line.

2. The system according to claim 1, wherein the conveying system and the supply interruption system are designed such that a fluid flow in the fluid circuit including the treatment unit can be adjusted at a predetermined flow rate.

3. The system according to claim 2, wherein the control unit is designed such that,
    in a first work step of a first work cycle of successive work cycles, the balancing chamber is filled via the first supply line with fluid from the fluid source, fluid thereby being displaced out of the balancing chamber via the first discharge line into the drain, whereby fluid circulates in the fluid circuit including the treatment unit completely bypassing the balancing chamber, and,
    in a second work step of the successive work cycles, fluid is carried away from the balancing chamber via the second discharge line and fluid is fed to the balancing chamber via the second supply line, whereby fluid circulates in the fluid circuit including the treatment unit.

4. The system according to claim 2, wherein the supply interruption system comprises:
    a first shut-off element disposed in the first supply line,
    a second shut-off element disposed in the first discharge line,
    a third shut-off element disposed in the second discharge line,
    a fourth shut-off element disposed in the second supply line.

5. The system according to claim 4, wherein the control unit is designed such that the first and second shut-off elements are opened and the third and fourth shut-off elements are closed in a first work step of a first work cycle of successive work cycles, the first and third pumps being in operation, and
    the first and second shut-off elements are closed and the third and fourth shut-off elements are opened in a second work step of successive work cycles, the second and third pumps being in operation.

6. The system according to claim 5, wherein the control unit is designed such that the second and third pumps are operated in different delivery modes in the second work step.

7. The system according to claim 5, wherein the control unit is designed such that the third pump is operated in the second work step at a delivery rate which is greater than the delivery rate of the second pump.

8. The system according to claim 1, wherein the second discharge line comprises, in the flow direction, the first and second sections and the second supply line comprises, in the flow direction, a first and second section, whereby one connection of the bypass line is connected to the junction point between the first and second section of the second discharge line and the other connection of the bypass line is connected to the junction point between the first and second section of the second supply line.

9. The system according to claim 1, wherein the supply interruption system comprises:

a first shut-off element disposed in the first supply line,
a second shut-off element disposed in the first discharge line,
a third shut-off element disposed in the second discharge line,
a fourth shut-off element disposed in the second supply line.

10. The system according claim 9, wherein the supply interruption system comprises a fifth shut-off element which is disposed in the bypass line.

11. An apparatus for extracorporeal blood treatment comprising the system according to claim 1.

12. The extracorporeal blood treatment apparatus according to claim 11, further comprising:

a blood treatment unit, wherein the extracorporeal blood treatment apparatus is a dialysis apparatus and the blood treatment unit is a dialyzer.

* * * * *